(12) United States Patent
Ellsworth et al.

(10) Patent No.: US 8,308,792 B2
(45) Date of Patent: Nov. 13, 2012

(54) DEVICE FOR LOADING SELF-EXPANDING STENTS

(75) Inventors: Thomas D. Ellsworth, Easton, PA (US); Israel James Jessop, Berkeley Heights, NJ (US); Dennis Vaughan, North Miami, FL (US)

(73) Assignee: Cordis Corporation

( * ) Notice: Subject to any disclaimer, the term of this patent is extended or adjusted under 35 U.S.C. 154(b) by 700 days.

(21) Appl. No.: 12/129,933

(22) Filed: May 30, 2008

(65) Prior Publication Data

US 2009/0299451 A1    Dec. 3, 2009

(51) Int. Cl.
*A61F 2/06* (2006.01)

(52) U.S. Cl. .................................... 623/1.11

(58) Field of Classification Search .............. 606/108, 606/194–195, 198, 200; 623/1.1, 1.11–1.12, 623/1.2, 1.23
See application file for complete search history.

(56) References Cited

U.S. PATENT DOCUMENTS

| 5,556,414 A * | 9/1996 | Turi .................................. 623/1.11 |
| 7,172,620 B2 * | 2/2007 | Gilson ............................. 623/1.11 |
| 2005/0234502 A1 * | 10/2005 | Gilson et al. ................. 606/200 |

* cited by examiner

*Primary Examiner* — Ryan Severson
*Assistant Examiner* — Ashley Cronin

(57) ABSTRACT

A device upon which a self-expanding stent may be crimped is utilized to safely load the self-expanding stent directly into a transfer tube or a delivery tube. The device comprises a compliant member, an expandable member, an expansion member and a retrieval member.

3 Claims, 8 Drawing Sheets

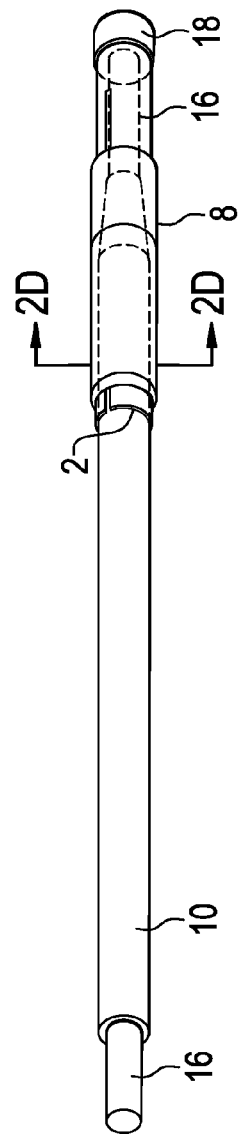
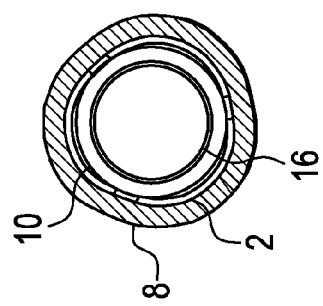

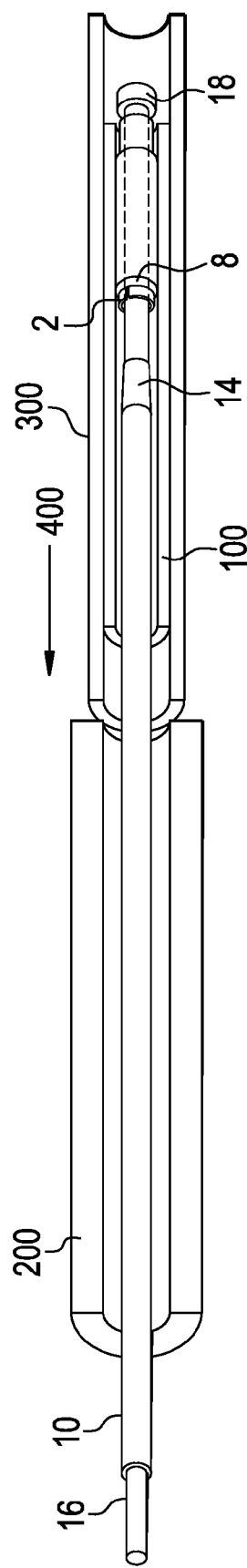

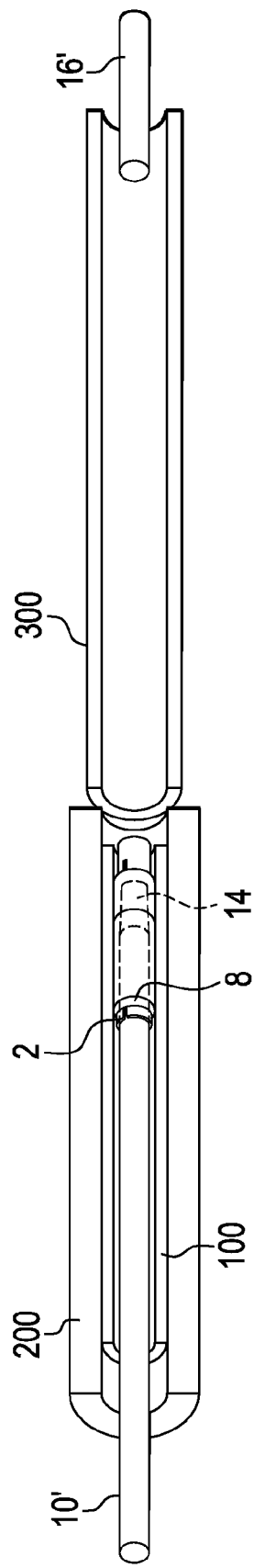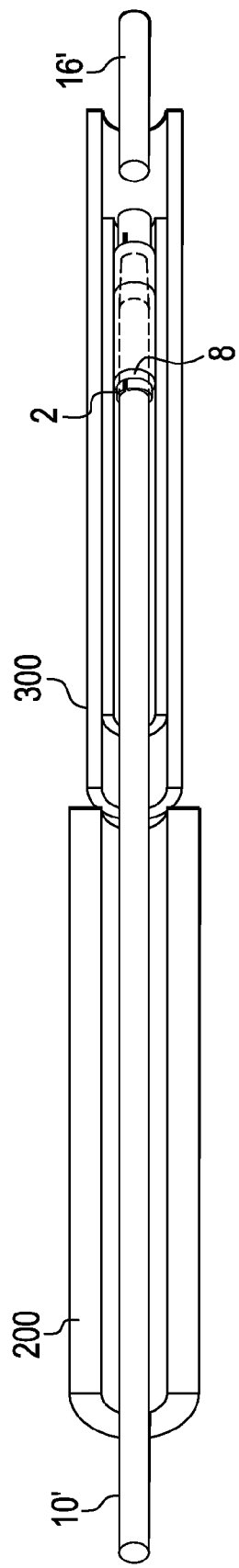

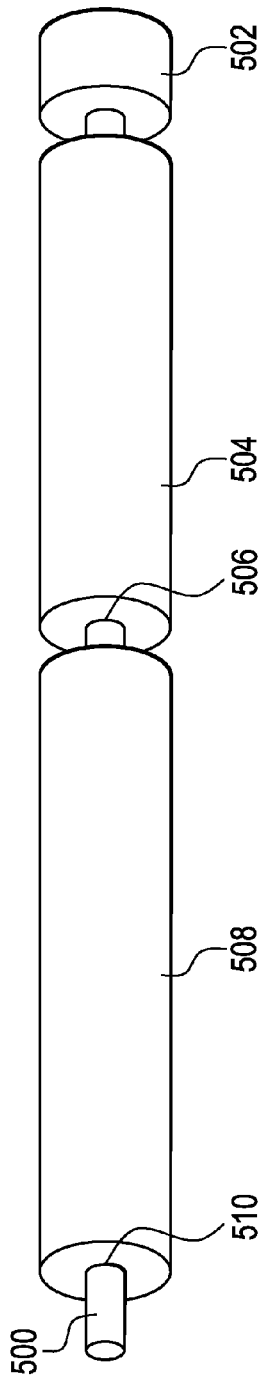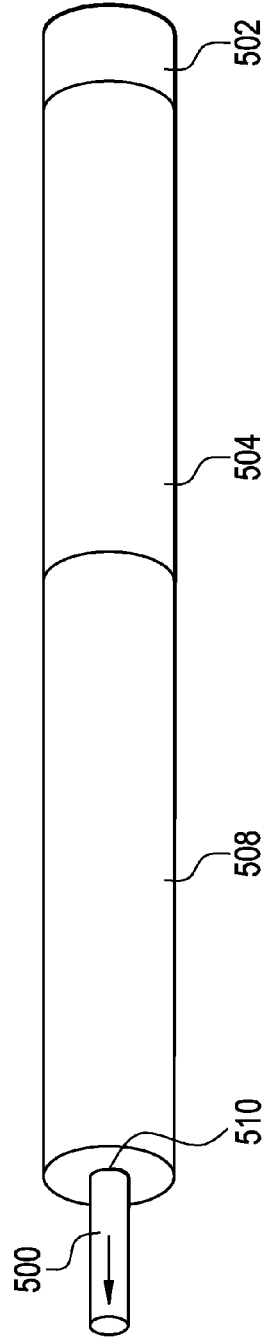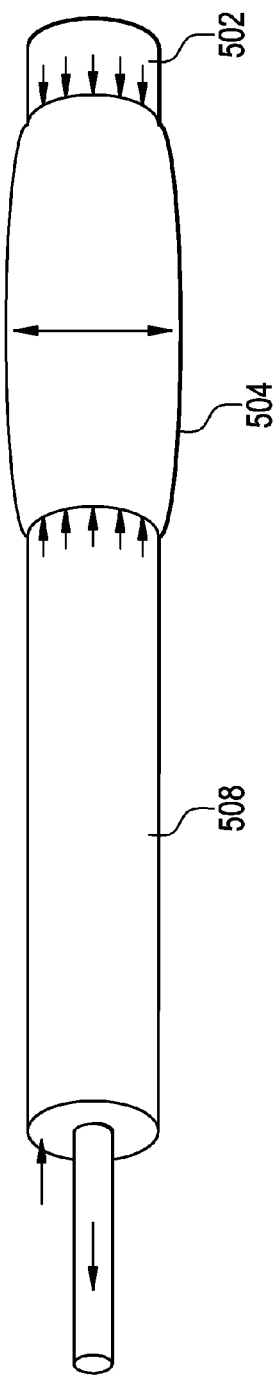

DEVICE FOR LOADING SELF-EXPANDING STENTS

BACKGROUND OF THE INVENTION

1. Field of the Invention

The present invention relates to devices for loading self-expanding stents into transfer tubes or delivery tubes, and more particularly to a reusable, expanding mandrel loading device for loading, crimping and transferring self-expanding stents into either a transfer tube or a delivery tube.

2. Discussion of the Related Art

Stents and similar devices are designed for radial stiffness and longitudinal flexibility. The combination may present certain difficulties when loading the stent into a delivery device or a transfer device.

Typically, a stent is loaded in the crimped state. Devices for loading stents generally provide a means for inserting the stent into a transfer tube or delivery tube while trying to prevent movement of the stent which may potentially cause damage to the stent.

Accordingly, there is a need for a device which securely holds the stent in position while being loaded and then releases the stent when loading is complete.

SUMMARY OF THE INVENTION

The loading device of the present invention overcomes the difficulties associated with loading self-expanding stents as briefly described above.

In accordance with one aspect, the present invention is directed to a loading device for self expanding stents. The loading device for self-expanding stents comprising a compliant member configured for seating a self-expanding stent and having a lumen therethrough; an expandable member, a portion of which is removably mounted within the lumen of the complaint member, the expandable member being configured to move from an unexpanded diameter to an expanded diameter and from an expanded diameter to an unexpanded diameter, the expandable member having a lumen therethrough, an expansion member configured to slidably engage the lumen of the expandable member, the expansion member having a tapered end with a diameter less than that of lumen of the expandable member and a main section with a diameter greater than that of the lumen of the expandable member, the expansion member having a lumen therethrough, and a retrieval member configured to slidably engage the lumen of the expansion member.

The present invention is directed to a device upon which a self-expanding stent may be crimped and then loaded into a transfer tube or a delivery tube. The device is simple to utilize, minimizes the potential for damage to the self-expanding stent upon loading and may be repeatedly utilized. In addition, the elements of the device are easily fabricated and easily assembled into the final device.

BRIEF DESCRIPTION OF THE DRAWINGS

The foregoing and other features and advantages of the invention will be apparent from the following, more particular description of preferred embodiments of the invention, as illustrated in the accompanying drawings.

FIGS. 2A, 2B, 2C and 2D are diagrammatic representations of two additional elements of the exemplary loading device in accordance with the present invention.

FIGS. 3A, 3B, 3C and 3D are diagrammatic representations of a loading procedure in accordance with the present invention.

FIGS. 4A, 4B, 4C and 4D are diagrammatic representations of an alternate loading procedure in accordance with the present invention.

FIGS. 5A, 5B and 5C are diagrammatic representations of an alternate exemplary embodiment of a loading device in accordance with the present invention.

DETAILED DESCRIPTION OF THE PREFERRED EMBODIMENTS

The present invention is directed to a device for loading self-expanding stents into transfer tubes or delivery tubes. The device facilitates the safe and efficient crimping and subsequent loading of crimped self-expanding stents into transfer tubes or delivery tubes. In addition, the device is reusable.

Figure 1A:
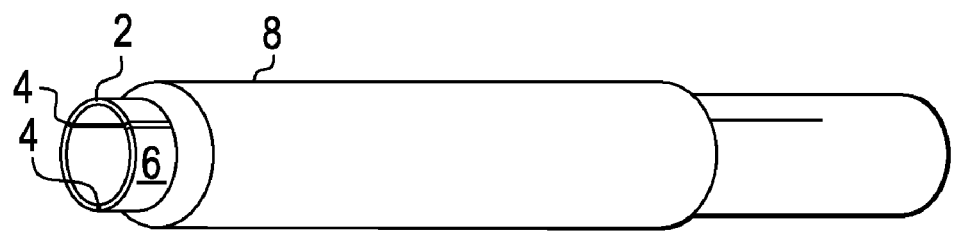
FIGS. 1A and 1B are diagrammatic representations of two elements of the exemplary loading device in accordance with the present invention.
Figure 1B:
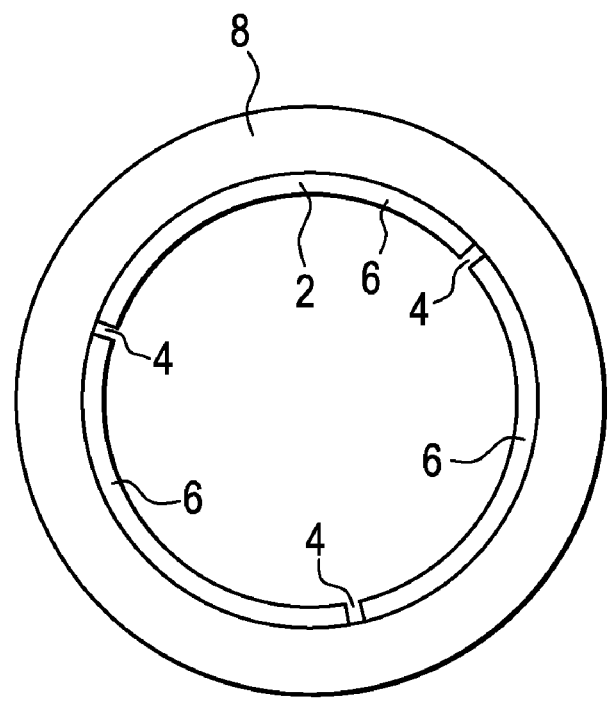
Figure 2A:
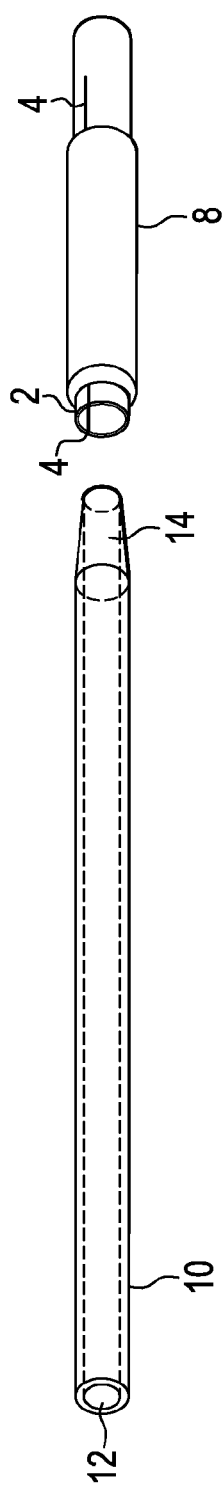
Figure 2B:
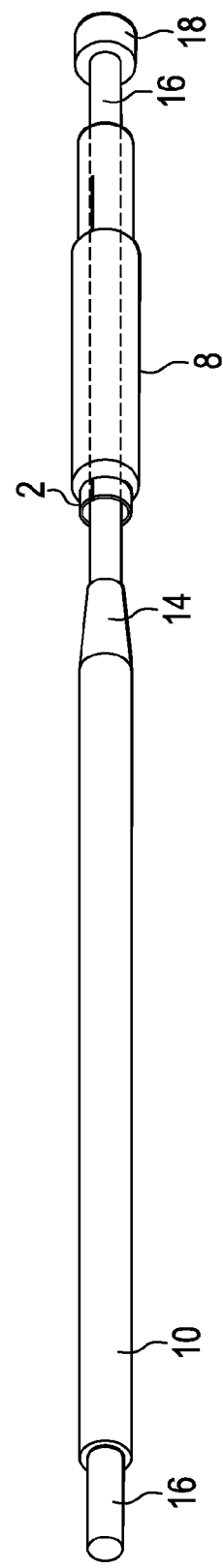
Figure 3A:
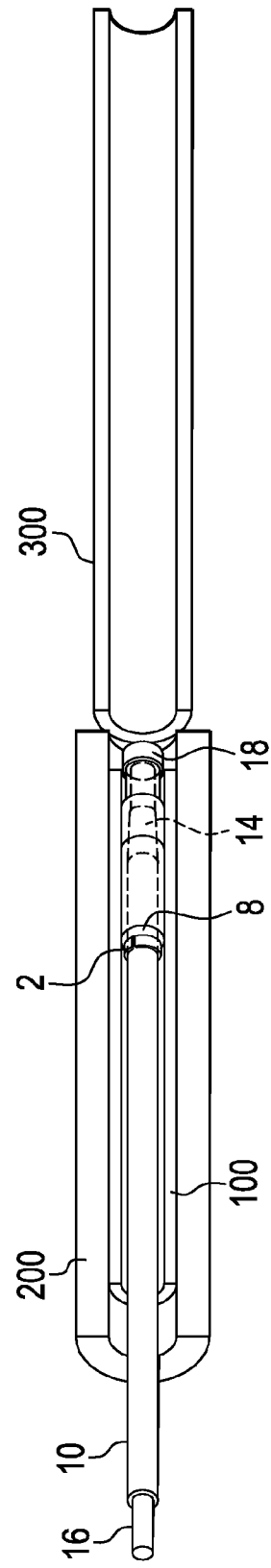
Figure 3B:
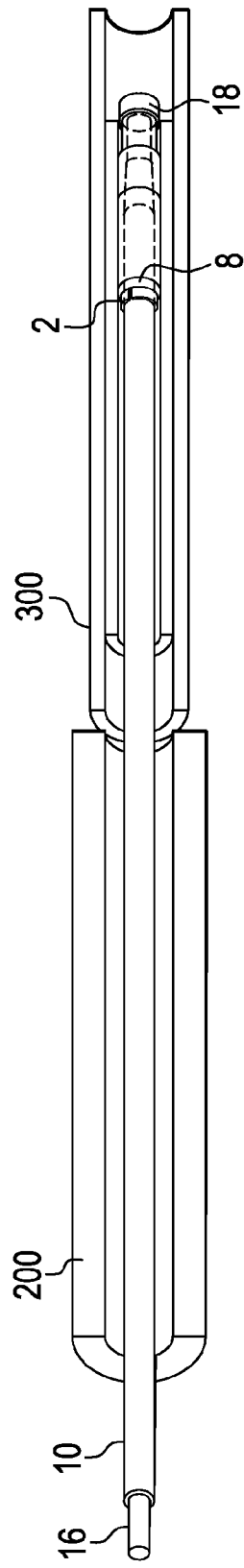
Figure 4C:
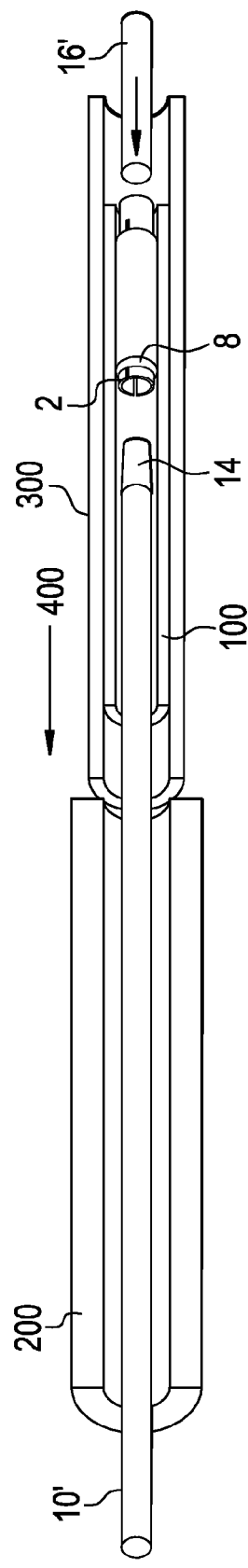
Figure 4D:
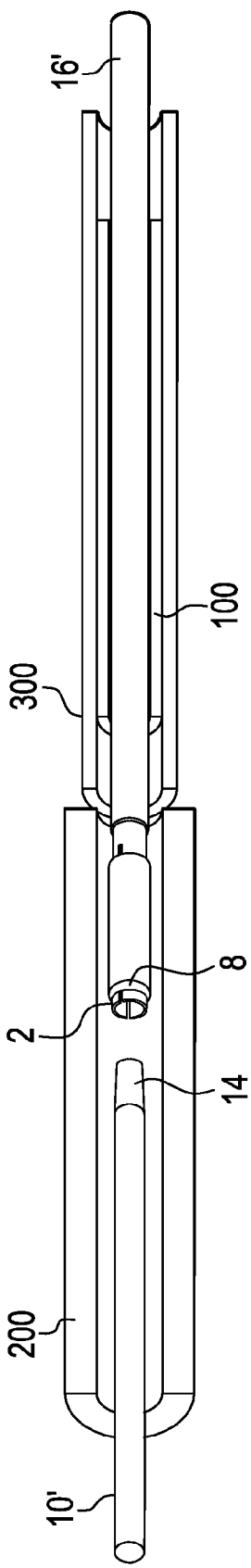

Referring to FIGS. 1A and 1B, there is illustrated two elements of the exemplary device for loading self-expanding stents into transfer or delivery tubes in accordance with the present invention. The first element is a collet 2 formed from a slot-cut metal tube and as such comprises a lumen extending therethrough. The slots 4 allow the collet 2 to expand as is described in detail subsequently. The collet 2 may be fabricated from any suitable material, for example, a plastic tube, that is stiff enough to withstand about fifteen to about twenty pounds compression force without buckling and elastic enough for the collet leaves 6 to expand and contract repeatedly without permanent deformation or fatigue. In addition, the inner surface should preferably be smooth enough for repeated sliding contact with an expansion mandrel as is described subsequently. In the exemplary embodiment, the collet 2 may be formed from stainless steel or a nickel-titanium alloy. Although illustrated as a three leaf collet with the slots being spaced about one hundred-twenty degrees apart, any suitable design may be utilized.

The second element is a compliant sleeve 8 that fits substantially concentrically around the slotted portion of the collet 2. As is explained in detail subsequently, the complaint sleeve 8 is the element upon which the stent is positioned and crimped, and as such various length compliant sleeves 8 may be utilized to accommodate stents of different lengths. The compliant sleeve 8 is preferably constructed from any biocompatible material that exhibits durability, i.e. no generation of particulate matter, and enough elasticity to recover about thirty-five percent circumferential strain. Exemplary materials include polyurethane or polyisoprene.

Referring now to FIGS. 2A, 2B, 2C and 2D, there is illustrated the collet 2, the compliant sleeve 8 and an additional two elements of the exemplary device for loading self-expanding stents into transfer or delivery tubes in accordance with the present invention. The third element is an expansion mandrel 10. In this exemplary embodiment, the expansion mandrel 10 comprises a substantially cylindrical member having a lumen 12 extending though its entire length and a tapered end 14. The expansion mandrel 10 is oversized to expand the collet 2, but has the tapered end 14 for easily engaging the collet 2. Essentially, the expansion mandrel 10 has an outside diameter greater than the inside diameter of the collet 2. Accordingly, when the expansion mandrel 10 is pushed through the collet 2 as is explained in more detail subsequently, it expands the collet 2 and the compliant sleeve 8. The expansion mandrel 10 may be constructed from any suitable material.

The fourth element is a retrieval rod 16. The retrieval rod 16 comprises a substantially cylindrical rod having a diameter and finish that allows it to easily slide within the lumen 12 of the expansion mandrel 10. The retrieval rod 16 also comprises a stop 18 on one end that prevents it from moving into the collet 2 when utilized as is explained in detail subsequently.

The four elements described above are assembled as described below. The compliant sleeve 8 is positioned over the collet 2. The retrieval rod 16 is positioned through the collet 2 and the lumen 12 of the expansion mandrel 10. With these elements assembled, an operator pulls the end of the retrieval rod 16 while holding the expansion mandrel 10 so that the stop 18 ferries the collet 2 onto the tapered end 14 of the expansion mandrel 10 and the collet 2 and the compliant sleeve 8 expand to its fully expanded diameter as illustrated specifically in FIGS. 2C and 2D.

With the device in its expanded state, the crimping and loading of the self-expanding stent may proceed. FIGS. 3A, 3B, 3C and 3D illustrate the exemplary procedure. The device which comprises the collet 2, the compliant sleeve 8, the expansion mandrel 10 and the retrieval rod 16 is illustrated with a stent 100 loaded onto the compliant sleeve 8 and positioned within a crimping device 200. Although illustrated as a partial cylindrical tube, the stent 100 may comprise any type of self-expanding stent. In addition, although the crimping device 200 is also illustrated as a partial cylindrical tube, any device for crimping a stent may be utilized in conjunction with the device of the present invention. The stent 100 is crimped onto the compliant sleeve 8 such that outside diameter of the expanded compliant sleeve 8 engages the inside diameter of the crimped stent 100. With the stent 100 crimped onto the device, it is ready for loading into a transfer tube or delivery tube 300.

In order to load the stent 100 into the transfer tube or delivery tube 300, the end of the expansion mandrel 10 is pushed into the transfer tube 300, thereby carrying all of the other elements of the device and the crimped stent 200 with it. The device allows for the loading of the self-expanding stent 100 directly from the crimping device 200 to the delivery or transfer tube 300. Once the crimped stent 200 is positioned within the transfer tube 300 at the desired location, the device may be removed.

To remove the device from the transfer tube 300, the expansion mandrel 10 is pulled rather than the retrieval rod 16. By pulling the expansion mandrel 10 in the direction of arrow 400 and holding the retrieval rod 10, the expansion mandrel 10 may be extricated from within the collet 2 and the complaint sleeve 8. With the expansion mandrel 10 removed, the collet 2 and the compliant sleeve 8 return to their unexpanded diameters, thereby freeing the stent 100 from the device. The loading device may now be removed by pulling on the retrieval rod so that the stop 18 pulls the remaining elements of the device with it. Once removed, the loading device may be repositioned for the next loading cycle and the stent 100 is retained in the transfer or delivery tube 300.

It is important to note that any number of biocompatible materials may be utilized in conjunction with the fabrication of the elements of the device. However, it is also important to note, that the various elements may also be coated with any number of biocompatible materials to facilitate the operation of the device, for example, lubricious coatings may be utilized to reduce friction.

In one alternate exemplary embodiment, the expansion mandrel 10 illustrated in FIGS. 2A, 2B, 2C and 2D as well as FIGS. 3A, 3B, 3C and 3D may comprise a solid member rather than an element having a lumen extending therethrough. In all other respects, the solid member expansion mandrel would be substantially identical. As before, the solid member expansion mandrel has an outside diameter greater than the inside diameter of the collet 2. Accordingly, when the solid member expansion mandrel is pushed through the collet 2, it expands the collet 2 and the compliant sleeve 8. The solid member expansion mandrel may be constructed from any suitable material.

Given that the solid member expansion mandrel comprises no lumen, the retrieval rod 16 described above can no longer be utilized. In its place, a simple rod, may be utilized to push the solid member expansion mandrel from the collet 2 and compliant sleeve 8 from the end which made contact with the stop 18 described in the previous exemplary embodiment. The simple rod may be constructed from any suitable material. FIGS. 4A, 4B, 4C and 4D illustrate this exemplary embodiment. The expansion mandrel 10' has no lumen like expansion mandrel 10 and the retrieval rod 16' is a simple rod with no stop.

In another alternate exemplary embodiment, the individual collet 2 and compliant sleeve 8 may be replaced with a single element comprising the properties of both individual elements. Essentially, the collet 2 and compliant sleeve 8 may be replaced with a polymeric tube that is expanded by either of the expansion mandrels described above and then removed to allow the polymeric tube to collapse and disengage from the stent 100.

FIGS. 5A, 5B and 5C illustrate yet another exemplary embodiment of a device for loading self-expanding stents into transfer or delivery tubes in accordance with the present invention. In this exemplary embodiment, the device comprises a substantially cylindrical rod 500 having a stop 502 on one end thereof. The rod 500 may comprise any suitable material such as a metallic or polymeric material. A compressible sleeve 504 having a lumen 506 is positioned around the rod 500. The compressible sleeve 504 is slidable along the rod 500, but is maintained thereon by the stop 502. The compressible sleeve 504 may be constructed from any suitable material such as a polymeric material. A compressive member 508 having a lumen 510 is also mounted on the rod 500. The compressive member 508 is also slidable along the rod 500 and may be formed from any suitable material that is less complaint than the compressible sleeve 504 for the reasons set forth below.

In operation, the compressive member 508 is pushed against the compressible sleeve 504 such that it is forced into the stop 502. Continual pressure caused by either pulling the rod 500 or pushing the compressive member 508 causes the compressible sleeve 504 to expand in diameter after which the stent may be loaded as described above. As with the previous embodiments, once loading is complete, the pressure can be released, and the diameter of the compressible sleeve 504 would return to its original diameter.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A device for loading, crimping and transferring crimped self-expanding stents comprising:

a compliant sleeve configured for seating a self-expanding stent and having a lumen therethrough;

a collet, a portion of which is removably mounted within the lumen of the compliant sleeve, the collet being configured to move from an unexpanded diameter to an expanded diameter and from the expanded diameter to the unexpanded diameter, the collet having a lumen therethrough, the collet also comprising at least one longitudinally oriented slot;

an expansion mandrel configured to slidably engage the lumen of the collet, the expansion mandrel having a tapered end with a diameter less than that of the diameter of the lumen of the collet and a main section with a diameter greater than that of the diameter of the lumen of the collet, the expansion mandrel having a lumen therethrough, and a retrieval rod configured to slidably engage the lumen of the expansion mandrel and the lumen of the collet, the retrieval rod having a stop with a diameter greater than that of the collet on one end thereof, wherein the expansion mandrel and the retrieval rod are configured for relative movement to force the expansion mandrel into the collet such that the main section of the expansion mandrel expands the collet and the sleeve and to remove the expansion mandrel from the collet.

2. The loading device for self-expanding stents according to claim 1, wherein the compliant sleeve comprises an elastomeric sleeve.

3. The loading device for self-expanding stents according to claim 1, wherein the compliant sleeve comprises a polymeric sleeve.

* * * * *